United States Patent
Kim et al.

(10) Patent No.: US 11,384,035 B2
(45) Date of Patent: Jul. 12, 2022

(54) OLIGOMER PREPARATION METHOD AND OLIGOMER PREPARATION DEVICE

(71) Applicant: LG CHEM, LTD., Seoul (KR)

(72) Inventors: Eun Kyo Kim, Daejeon (KR); Mi Kyung Kim, Daejeon (KR); Joon Ho Shin, Daejeon (KR); Hye Bin Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 17/424,426

(22) PCT Filed: Aug. 7, 2020

(86) PCT No.: PCT/KR2020/010466
§ 371 (c)(1),
(2) Date: Jul. 20, 2021

(87) PCT Pub. No.: WO2021/033971
PCT Pub. Date: Feb. 25, 2021

(65) Prior Publication Data
US 2022/0089510 A1  Mar. 24, 2022

(30) Foreign Application Priority Data

Aug. 21, 2019 (KR) .................. 10-2019-0102511
Jul. 29, 2020 (KR) .................. 10-2020-0094665

(51) Int. Cl.
*C07C 2/08* (2006.01)
*B01D 3/14* (2006.01)
(Continued)

(52) U.S. Cl.
CPC ............... *C07C 2/08* (2013.01); *B01D 3/143* (2013.01); *C07C 7/005* (2013.01); *C07C 7/04* (2013.01)

(58) Field of Classification Search
None
See application file for complete search history.

(56) References Cited

U.S. PATENT DOCUMENTS 2,411,264 A * 11/1946 Hachmuth ............... C07C 7/04
203/84
2007/0185362 A1   8/2007 Lattner et al.
(Continued)

FOREIGN PATENT DOCUMENTS

JP   2000-264919 A   9/2000
JP   2014-12665 A    1/2014
(Continued)

*Primary Examiner* — Ali Z Fadhel
(74) *Attorney, Agent, or Firm* — Dentons US LLP

(57) ABSTRACT

Provided are a method for preparing an oligomer and an apparatus for preparing the same. The method for preparing an oligomer including: supplying a feed stream including a monomer to a reactor to perform an oligomerization reaction; supplying a first discharge stream from the reactor to a first separation device and supplying a second discharge stream from the reactor to a second separation device; recovering the monomer as an upper discharge stream from the second separation device and supplying a lower discharge stream from the second separation device to a third separation device; and supplying an upper discharge stream from the third separation device to the second separation device.

12 Claims, 2 Drawing Sheets

(51) Int. Cl.
*C07C 7/04* (2006.01)
*C07C 7/00* (2006.01)

(56) References Cited

U.S. PATENT DOCUMENTS

| | | |
|---|---|---|
| 2009/0149684 A1 | 6/2009 | Randolph et al. |
| 2013/0102826 A1* | 4/2013 | Lattner .................... C07C 2/08 585/510 |
| 2013/0296483 A1 | 11/2013 | Yokota et al. |
| 2016/0368834 A1 | 12/2016 | Nyce et al. |
| 2017/0190637 A1 | 7/2017 | Emoto |

FOREIGN PATENT DOCUMENTS

| | | |
|---|---|---|
| JP | 2016-531165 A | 10/2016 |
| KR | 10-2012-0055646 A | 5/2012 |
| KR | 10-2012-0123131 A | 11/2012 |
| KR | 10-2018-0082573 A | 7/2018 |
| WO | 2012/039838 A2 | 3/2012 |
| WO | 2012/096159 A1 | 7/2012 |

* cited by examiner

[FIG. 1]
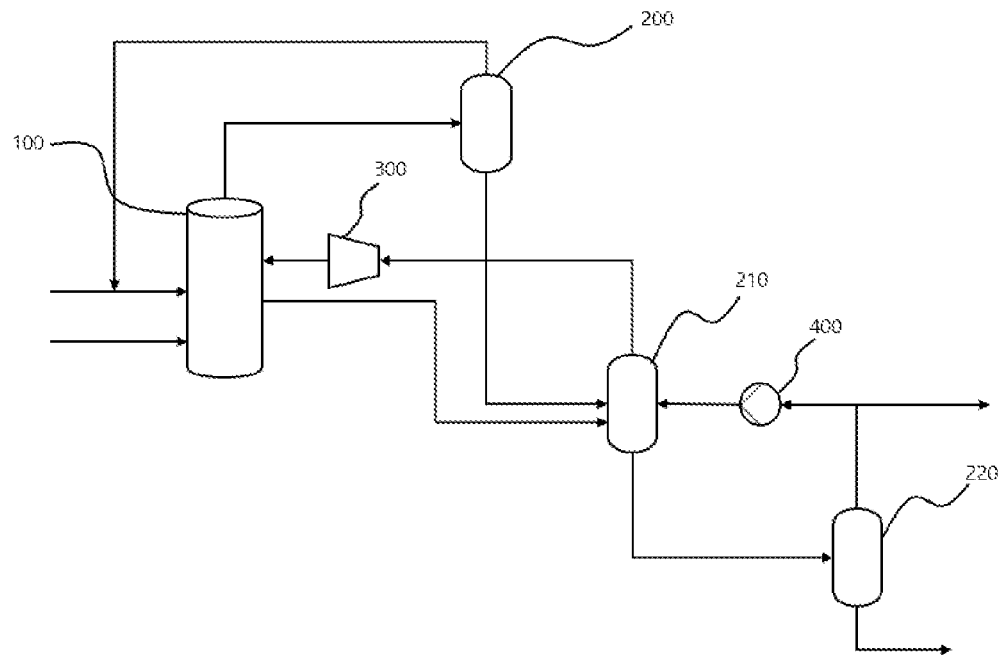
[FIG. 2]
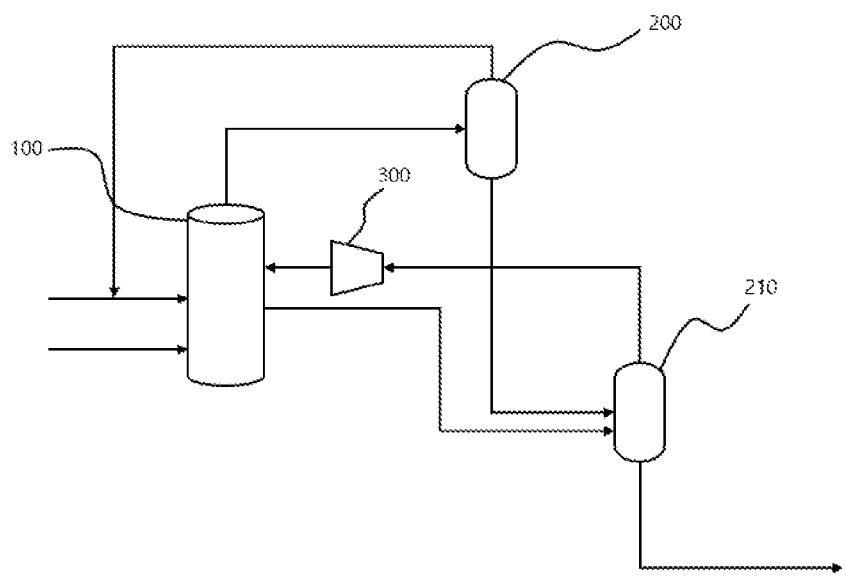

[FIG. 3]
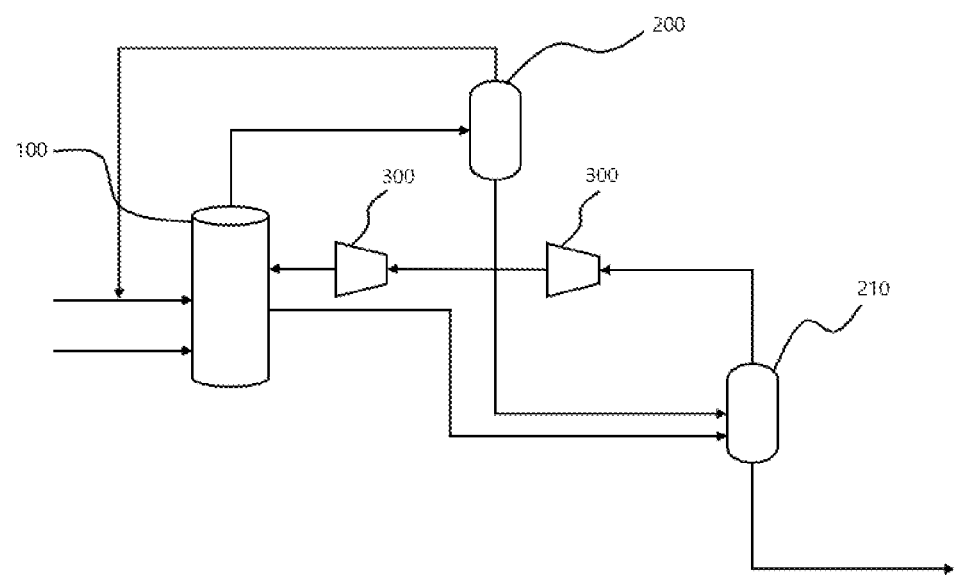

OLIGOMER PREPARATION METHOD AND OLIGOMER PREPARATION DEVICE

CROSS-REFERENCE TO RELATED APPLICATIONS

The present application is a National Phase entry pursuant to 35 U.S.C. § 371 of International Application No. PCT/KR2020/010466, filed on Aug. 7, 2020, and claims the benefit of and priority to Korean Patent Application No. 10-2019-0102511, filed on Aug. 21, 2019 and Korean Patent Application No. 10-2020-0094665, filed on Jul. 29, 2020, the entire contents of which are incorporated by reference in their entirety for all purposes as if fully set forth herein.

TECHNICAL FIELD

The present invention relates to a method for preparing an oligomer and an apparatus for preparing an oligomer, and more particularly, to a method for preparing an oligomer and an apparatus for preparing an oligomer which efficiently recycle a monomer recovered in an oligomer production process.

BACKGROUND ART

An alpha-olefin is an important material which is used in comonomers, cleaning agents, lubricants, plasticizers, and the like and is commercially widely used, and in particular, 1-hexene and 1-octene are often used as the comonomer for adjusting the density of polyethylene in the production of linear low-density polyethylene (LLDPE).

The alpha-olefins such as 1-hexene and 1-octene are produced representatively by an oligomerization reaction of ethylene. The ethylene oligomerization reaction is performed by an oligomerization reaction (trimerization reaction or tetramerization reaction) of ethylene using ethylene as a reactant, and the product produced by the reaction includes unreacted ethylene as well as a multi-component hydrocarbon mixture including the desired 1-hexene and 1-octene. The product is subjected to a separation process by a distillation column, in which the unreacted ethylene is recovered and reused in the oligomerization reaction of ethylene.

In recovering unreacted ethylene, in order to decrease an amount of a product or a by-product such as a solvent in a unreacted ethylene stream to be recovered, a separation device such as a distillation column or a flash drum is used. Here, since there is a great difference in boiling points between the unreacted ethylene and the product, a difference between an upper portion temperature and a lower portion temperature of the separation device increases. The upper portion and lower portion temperatures of the separation device are determined by a pressure of the separation device, and when the pressure of the separation device is high, the upper portion and lower portion temperatures are raised, and when the pressure of the separation device is low, the upper portion and lower portion temperatures are lowered. In the case in which the pressure of the separation device is increased, when the pressure of the separation device is increased, an upper portion temperature of the separation device is raised so that it is easy to recover unreacted ethylene, but a lower portion temperature of the separation device is also raised so that decomposition and reaction of hydrocarbons such as a product and a solvent may be promoted, thereby lowering a production yield of the product. However, in the case in which the pressure of the separation device is decreased, a side reaction of hydrocarbons may be suppressed, but the upper portion temperature of the separation device is lowered, and thus, additional configurations such as using a refrigerant at a low temperature when recovering unreacted ethylene or installing a compressor having a high compression ratio are required, and in this case, process costs may be increased.

As such, a conventional method of recovering unreacted ethylene to reuse it in the oligomerization reaction has problems of having high investment costs and being economically infeasible, for example, having a decreased production yield of the product, using a refrigerant at a very low temperature, installing a compressor having a high compression ratio, or the like.

DISCLOSURE

Technical Problem

In order to solve the problems described in the Background Art, an object of the present invention is to provide a method for preparing an oligomer and an apparatus for preparing an oligomer having reduced investment costs.

That is, an object of the present invention is to provide a method for preparing an oligomer and an apparatus for preparing an oligomer in which in an oligomer production process, in recovering unreacted ethylene to reuse it in an oligomerization reaction, investment costs are reduced, economic feasibility is improved, and a decrease in a production yield can be prevented since there is no need to use a refrigerant at a very low temperature or install a compressor having a high compression ratio.

Technical Solution

In one general aspect, a method for preparing an oligomer includes: supplying a feed stream including a monomer to a reactor to perform an oligomerization reaction; supplying a first discharge stream from the reactor to a first separation device and supplying a second discharge stream from the reactor to a second separation device; recovering the monomer as an upper discharge stream from the second separation device and supplying a lower discharge stream from the second separation device to a third separation device; and supplying an upper discharge stream from the third separation device to the second separation device.

In another general aspect, an apparatus for preparing an oligomer includes: a reactor for oligomerizing a feed stream including a supplied monomer, supplying a first discharge stream to a first separation device, and supplying a second discharge stream to a second separation device; a first separation device for being supplied with the first discharge stream from the reactor; a second separation device for being supplied with the second discharge stream from the reactor to recover the monomer as an upper discharge stream and to supply a lower discharge stream to a third separation device; and a third separation device for being supplied with the lower discharge stream from the second separation device to supply an upper discharge stream to the second separation device.

Advantageous Effects

According to the method for preparing an oligomer and the apparatus for preparing an oligomer of the present invention, in recovering the unreacted monomer, the second separation device is operated at a high pressure, the third separation device to which the lower discharge stream from the second separation device is connected is operated at a low pressure, the upper discharge stream from the third separation device is supplied to the second separation device to connect the second separation device and the third separation device, thereby concentrating a by-product having a boiling point higher than the monomer and lower than the oligomer product in a lower flow of the second separation device. Therefore, the second separation device is operated at a high pressure to lower the lower portion temperature while maintaining the upper portion temperature high, thereby suppressing the side reaction of hydrocarbons while efficiently recovering the monomer.

In addition, the by-product concentrated from a circulated flow of the second separation device and the third separation device can be removed to decrease a loss of the monomer.

DESCRIPTION OF DRAWINGS

FIG. 1 is a process flowchart of a method for preparing an oligomer according to an exemplary embodiment of the present invention.

FIGS. 2 and 3 are process flowcharts of a method for preparing an oligomer according to the Comparative Examples, respectively.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

In the present invention, the term "stream" may refer to a fluid flow in a process, or may refer to a fluid itself flowing in a pipe. Specifically, the "stream" may refer to both a fluid itself flowing in a pipe connecting each apparatus and a fluid flow. In addition, the fluid may refer to a gas or a liquid.

Hereinafter, the present invention will be described in more detail for better understanding the present invention.

According to the present invention, a method for preparing an oligomer is provided. As the method for preparing an oligomer, a method for preparing an oligomer including: supplying a feed stream including a monomer to a reactor to perform an oligomerization reaction; supplying a first discharge stream from the reactor to a first separation device and supplying a second discharge stream from the reactor to a second separation device; recovering the monomer as an upper discharge stream from the second separation device and supplying a lower discharge stream from the second separation device to a third separation device; and supplying an upper discharge stream from the third separation device to the second separation device, can be provided.

According to an exemplary embodiment of the present invention, in a step of supplying a feed stream including a monomer to a reactor to perform an oligomerization reaction, the feed stream including the monomer can be supplied to the reactor, and the oligomerization reaction of the monomer can be performed in a liquid phase in a lower portion of the reactor. The oligomerization reaction may refer to a reaction in which a monomer is oligomerized. The oligomerization may be referred to as trimerization or tetramerization depending on the number of monomers to be polymerized, and these are collectively called multimerization.

According to an exemplary embodiment of the present invention, the monomer can be ethylene and the oligomer can be an alpha-olefin. The alpha-olefin is an important material which is used in comonomers, cleaning agents, lubricants, plasticizers, and the like and is commercially widely used, and in particular, 1-hexene and 1-octene are often used as a comonomer for adjusting the density of polyethylene in the production of linear low-density polyethylene (LLDPE). The alpha-olefin such as 1-hexene and 1-octene can be produced by, for example, a trimerization reaction or tetramerization reaction of ethylene.

According to an exemplary embodiment of the present invention, the step of performing the oligomerization reaction of the monomer can be performed in a reactor appropriate for a continuous process, and preferably performed under a reaction system including one or more reactors selected from the group consisting of a continuous stirred tank reactor (CSTR) and a plug flow reactor (PFR).

According to an exemplary embodiment of the present invention, the oligomerization reaction of the monomer can be performed by a homogeneous liquid phase reaction, a slurry reaction having a catalyst system in a partially or entirely not dissolved form, a two-phase liquid/liquid reaction, or a bulk phase reaction or gas phase reaction in which the product acts as a main medium, in the presence or absence of a solvent, by applying the reaction system and a common contact technology. Preferably, the step of performing the oligomerization reaction of the monomer can be performed in the homogeneous liquid phase reaction.

According to an exemplary embodiment of the present invention, the step of performing the oligomerization reaction can be performed at a temperature of 10° C. to 180° C., 30° C. to 150° C., or 50° C. to 120° C. In addition, the step of performing the oligomerization reaction can be performed under a pressure of 15 bar to 100 bar, 20 bar to 80 bar, or 25 bar to 60 bar. When ethylene is oligomerized within the temperature range and the pressure range, a selectivity to a desired alpha-olefin can be excellent, a by-product amount can be decreased, the operational efficiency of a continuous process can be increased, and the costs can be reduced.

According to an exemplary embodiment of the present invention, the feed stream including the monomer can include a gaseous monomer and a solvent.

The gaseous monomer included in the feed stream can be supplied as, for example, a feed stream including an ethylene monomer separated from a naphtha cracking center (NCC) process as it is or after being subjected to a storage step. In addition, the gaseous monomer can include a stream recovered in the oligomer production process.

The solvent included in the feed stream can be supplied to the reactor as the feed stream. In some cases, as the solvent, a solvent recovered after being used in an oligomerization process can be reused.

According to an exemplary embodiment, in a step of supplying a first discharge stream from the reactor to a first separation device and supplying a second discharge stream from the reactor to a second separation device, a common distillation column can be used as the separation device.

According to the exemplary embodiment of the present invention, the first discharge stream can be a stream including the gaseous monomer. The first separation device can supply the upper discharge stream including the gaseous monomer to the reactor and supply the lower discharge stream including the liquid monomer to the second separation device. Here, the upper discharge stream from the first separation device can be mixed with the gaseous monomer stream which is separately supplied to the reactor in a mixer and supplied to the reactor, or can be separately supplied to the reactor.

According to an exemplary embodiment of the present invention, the second discharge stream from the reactor can be supplied to the second separation device and be separated into the upper discharge stream including the gaseous monomer and the lower discharge stream including an oligomer product, a by-product, and the solvent.

The gaseous monomer recovered from the second separation device as the upper discharge stream can be supplied to the reactor. Here, the upper discharge stream from the second separation device can be mixed with the gaseous monomer stream which is separately supplied to the reactor and the upper discharge stream from the first separation device in a mixer and supplied to the reactor, or can be separately supplied to the reactor.

The lower discharge stream from the second separation device can be supplied to the third separation device, and be separated into a liquid lower discharge stream including the oligomer and the solvent and a liquid upper discharge stream including a C4 compound as a by-product, in the third separation device. Here, the C4 compound can include 1-butene (1-C4).

A content of the C4 compound included in the upper discharge stream from the third separation device can be 70 wt % or more. For example, the content of the C4 compound included in the upper discharge stream from the third separation device can be in a range of 70 wt % to 99 wt %, 80 wt % to 95 wt %, or 85 wt % to 90 wt %. As such, as the upper discharge stream from the third separation device including the C4 compound is supplied to the second discharge stream, the second separation device and the third separation device can have a circulation flow. Here, the C4 compound is supplied from the third separation device as the upper discharge stream to the second separation device, thereby concentrating the C4 compound having a lower boiling point than the oligomer product and the solvent in a lower portion of the second separation device. Thus, as the unreacted monomer is recovered in an upper portion of the second separation device, a lower portion temperature is lowered and the C4 compound concentrated as the lower discharge stream can be effectively removed.

The content of the C4 compound concentrated in the lower discharge stream from the second separation device can be 5 wt % to 40 wt %. For example, the content of the C4 compound included in the lower discharge stream from the second separation device can be in a range of 5 wt % to 40 wt %, 10 wt % to 30 wt %, or 13 wt % to 20 wt %.

The lower discharge stream from the second separation device including the concentrated C4 compound is supplied to the third separation device, and the upper discharge stream including 80 wt % or more of the C4 compound is discharged from the third separation device. Here, the C4 compound can be efficiently separated in a manner of furcating and recovering a part of the upper discharge stream from the third separation device without supplying it to the second separation device. For example, the upper discharge stream from the third separation device including the C4 compound at a high content can be partially purged to selectively recover the C4 compound.

The content of the C4 compound included in the part of the upper discharge stream from the third separation device can be 70 wt % or more. For example, the content of the C4 compound included in the part of the upper discharge stream from the third separation device can be in a range of 70 wt % to 99 wt %, 80 wt % to 95 wt %, or 85 wt % to 90 wt %. In addition, a content of the monomer included in the part of the upper discharge stream from the third separation device can be 5 wt % or less. For example, the content of the monomer included in the part of the upper discharge stream from the third separation device can be in a range of 0.01 wt % to 5 wt %, 0.1 wt % to 3 wt %, or 0.5 wt % to 2 wt %. As such, in the method for preparing an oligomer according to the present invention, the part of the upper discharge stream from the third separation device is purged while a loss of the monomer is minimized to 5 wt % or less, thereby selectively recovering the C4 compound which is the by-product in the process. Thus, a problem that in the conventional method for preparing an oligomer, due to a low selectivity to the C4 compound, when the C4 compound is removed by a method of purging a part of a unreacted monomer recover stream without a separate C4 separation step, the monomer is also removed with the C4 compound, resulting in a big loss of the monomer, has been solved.

A ratio of the content of the C4 compound included in the upper discharge stream from the third separation device to the content of the C4 compound included in the second discharge stream from the reactor can be 2 or more, 2 to 7, or 4 to 6. Here, the upper discharge stream from the third separation device can mean a stream which is discharged from an upper portion of the third separation device and supplied to the second separation device. A ratio of the content of the C4 compound included in the second discharge stream from the reactor to the content of the C4 compound included in the upper discharge stream from the third separation device can mean a concentration ratio of the concentrated C4 compound in the second discharge stream from the reactor while the second discharge stream from the reactor is supplied to the second separation device, passes through the third separation device, and is partially circulated. Specifically, the third separation device is installed at a rear end of the second separation device and the C4 compound is concentrated at a concentration ratio of 2 times or more the content of the C4 compound in the second discharge stream from the reactor, thereby obtaining an effect of lowering a boiling point of the lower discharge stream from the second separation device due to a low boiling point of the C4 compound, and thus, the lower portion temperature of the second separation device can be lowered while maintaining the pressure of the second separation device high. Specifically, when a material having a low boiling point has an increased concentration at the same pressure, an effect of lowering the boiling point of the mixture is shown, and thus, the boiling point of the lower discharge stream from the second separation device can be lowered by concentrating the C4 compound. Here, since a boiling point of the stream discharged from the distillation column can mean an operation temperature of the corresponding distillation column, the boiling point of the lower discharge stream from the second discharge stream can mean an operation temperature of the lower portion of the second separation device.

According to an exemplary embodiment of the present invention, the pressure in the second separation device can be operated at higher pressure than the pressure in the third separation device. Specifically, the lower discharge stream including the monomer is discharged to the third separation device while operating the second separation device at a high pressure, thereby lowering the lower portion temperature while maintaining the upper portion temperature of the second separation device high. Thus, the side reaction of hydrocarbons can be suppressed. Specifically, the upper portion temperature is maintained high and the lower portion temperature is lowered while operating the pressure of the second separation device high, thereby easily recovering the unreacted monomer in the upper portion and preventing occurrence of a side reaction in which the oligomer produced in the lower portion is decomposed or reacted with other materials to produce a by-product.

The pressure in the second separation device can be in a range of 12 bar to 25 bar, and the pressure in the third separation device can be in a range of 3 bar to 15 bar. For example, the pressure in the second separation device can be in a range of 12 bar to 25 bar, 13 bar to 23 bar, or 14 bar to 20 bar, and the pressure in the third separation device can be in a range of 3 bar to 15 bar, 4 bar to 13 bar, or 5 bar to 10 bar. The pressure in the second separation device or the third separation device is controlled to the range described above, thereby efficiently recovering the unreacted monomer without requiring a refrigerant at a low temperature or a compressor having a high compression ratio in the second separation device and the third separation device, and preventing occurrence of a side reaction in which the oligomer produced by the oligomerization reaction of the monomer in the lower portion of the second separation device is decomposed or reacted with other materials to produce a by-product.

The second separation device is operated at a high pressure, the lower discharge stream from the second separation device is supplied to the third separation device operated at a low pressure, and the C4 compound is concentrated in the lower portion of the second separation device from the circulation flow between the second separation device at a high pressure and the third separation device at a low pressure, thereby lowering the lower portion temperature while maintaining the upper portion temperature of the second separation device high. Specifically, the temperature of the lower discharge stream from the second separation device can be 130° C. to 200° C. For example, the temperature of the lower discharge stream from the second separation device can be 130° C. to 200° C., 140° C. to 190° C., or 150° C. to 180° C.

According to an exemplary embodiment of the present invention, in the lower discharge stream from the third separation device, the solvent and the oligomer can be separated by an additional separation process, and the separated solvent can be supplied to the reactor. In addition, the separated oligomer can be separated again into a trimer, a tetramer, and the like of the monomer by an additional separation process.

According to the present invention, an apparatus for preparing an oligomer is provided. As the apparatus for preparing an oligomer, an apparatus for preparing an oligomer including: a reactor for oligomerizing a feed stream including a supplied monomer, supplying a first discharge stream to a first separation device, and supplying a second discharge stream to a second separation device; a first separation device for being supplied with the first discharge stream from the reactor; a second separation device for being supplied with the second discharge stream from the reactor to recover the monomer as an upper discharge stream and to supply a lower discharge stream to a third separation device; and a third separation device for being supplied with the lower discharge stream from the second separation device to supply an upper discharge stream to the second separation device, can be provided.

According to an exemplary embodiment of the present invention, the apparatus for preparing an oligomer according to the present invention can be an apparatus for performing the process according to the method for preparing an oligomer described above.

According to an exemplary embodiment of the present invention, the apparatus for preparing an oligomer according to the present invention can be described with reference to the following FIG. 1. For example, the apparatus for preparing an oligomer includes a reactor 100 for oligomerizing a feed stream including a supplied monomer, and in the reactor 100, a first discharge stream including a gaseous monomer can be supplied to a first separation device 200 and a second discharge stream including a liquid monomer can be supplied to a second separation device 210.

According to an exemplary embodiment of the present invention, the feed stream supplied to the reactor 100 can include the monomer and the solvent. Specifically, the feed stream can include the gaseous monomer and the solvent. The feed stream including the gaseous monomer can include a gaseous monomer stream directly supplied to the reactor 100, the gaseous monomer recovered as the upper discharge stream from the first separation device 200, and the gaseous monomer recovered as the upper discharge stream from the second separation device 210. The gaseous monomer stream directly supplied to the reactor 100, the upper discharge stream from the first separation device 200 including the gaseous monomer, and the upper discharge stream from the second separation device 210 including the gaseous monomer can be separately supplied to the reactor 100, or supplied to the reactor 100 as a mixed discharge stream mixed in a mixer (not shown). The solvent can be separately supplied to the reactor 100, in which a solvent separated after being used in the process can be reused as the solvent.

According to an exemplary embodiment of the present invention, the first separation device 200 can be supplied with the first discharge stream from the reactor 100 and separated into the upper discharge stream including the gaseous monomer and the lower discharge stream including the liquid monomer. Here, the upper discharge stream from the first separation device 200 can be supplied to the reactor 100, and the lower discharge stream from the first separation device 200 can be supplied to the second separation device 210.

According to an exemplary embodiment of the present invention, the second separation device 210 can be supplied with the second discharge stream from the reactor 100 and the lower discharge stream from the first separation device 200 including the liquid monomer, and can be separated into the upper discharge stream including the gaseous monomer and the lower discharge stream including the oligomer product, the by-product, and the solvent. Here, the upper discharge stream from the second separation device 210 can be supplied to the reactor 100, and the lower discharge stream from the second separation device 210 can be supplied to the third separation device 220.

The upper discharge stream from the second separation device 210 can pass through a compressor 300 and be supplied to the reactor 100. Here, since the separation device 210 is operated at a high pressure of 12 bar to 20 bar, the apparatus is economical in that the compressor 300 having a relatively low compression ratio can be used. Therefore, process costs can be reduced as compared with the case of using the conventional compressor 300 having a high compression ratio.

The lower discharge stream from the second separation device 210 is supplied to the third separation device 220, and the upper discharge stream including the by-product including a C4 compound can be supplied to the second separation device 210. Here, the upper discharge stream from the third separation device 220 can be supplied to the second separation device 210 using a pump 400. Specifically, the upper discharge stream from the third separation device 220 is supplied to the second separation device 210 using the pump 400, and in this process, the pressure of the upper discharge stream from the third separation device 220 can be increased to the pressure of the second separation device 210.

A part of the upper discharge stream from the third separation device 220 is not supplied to the second separation device 210 but recovered. Specifically, the upper discharge stream from the third separation device 220 can be purged to recover a part of the stream including the C4 compound and the remaining stream can be supplied to the second separation device 210.

The lower discharge stream including the oligomer product and the solvent can be recovered from the third separation device 220. Here, the oligomer product and the solvent included in the lower discharge stream from the third separation device 220 can be separated by an additional separation device (not shown), and the separated solvent can be reused in the oligomer production process. In addition, example, in the case in which the oligomerization reaction is performed using an ethylene monomer as the monomer, the oligomer product can include 1-hexene and 1-octene. In this case, 1-hexene and 1-octene can be separated by an additional separation device (not shown) or separated by a separate process and used.

According to an exemplary embodiment of the present invention, in some cases, a condenser (not shown) can be further installed in an upper portion of any one or more of the first separation device 200, the second separation device 210, and the third separation device 220, and a reboiler (not shown) can be further installed in a lower portion thereof.

Hereinabove, the method for preparing an oligomer and the apparatus for preparing an oligomer according to the present invention have been described and illustrated in the drawings, but the description and the illustration in the drawings are the description and the illustration of only core constitutions for understanding of the present invention, and in addition to the process and apparatus described above and illustrated in the drawings, the process and the apparatus which are not described and illustrated separately may be appropriately applied and used for carrying out the method for preparing an oligomer and the apparatus for preparing an oligomer according to the present invention.

Hereinafter, the present invention will be described in more detail by the Examples. However, the following Examples are provided for illustrating the present invention. It is apparent to a person skilled in the art that various modifications and alterations may be made without departing from the scope and spirit of the present invention, and the scope of the present invention is not limited thereto.

EXAMPLES

Example 1

For the process flowchart illustrated in FIG. 1, the process was simulated using an Aspen Plus simulator from Aspen Technology, Inc. Here, the lower discharge stream from the second separation device 210 was a stream passing a reboiler (not shown), the upper discharge stream from the third separation device 220 was a stream passing a condenser (not shown), and the lower discharge stream from the third separation device 220 was a stream passing the reboiler (not shown). In addition, ethylene (C2) was supplied as the monomer at a reaction amount of 20,000 kg/hr or more, the reaction conditions of the reactor 100 were set at a temperature of 53° C. and a pressure of 30 bar, the operation pressure of the second separation device 210 was set at 15 bar, and the operation pressure of the third separation device 220 was set at 6 bar. The results are shown in the following Table 1.

TABLE 1

|  | Stream 1 | | Stream 2 | | Stream 3 | | Stream 4 | | Stream 5 | | Stream 6 | | Stream 7 | |
| --- | --- | --- | --- | --- | --- | --- | --- | --- | --- | --- | --- | --- | --- | --- |
| Temperature (° C.) | 53 | | 45 | | 160 | | 41 | | 43 | | 41 | | 161 | |
| Pressure (bar) | 30 | | 15 | | 15 | | 6 | | 15 | | 6 | | 6 | |
| Flow rate | kg/hr | wt % | kg/hr | wt % | kg/hr | wt % | kg/hr | wt % | kg/hr | wt % | kg/hr | wt % | kg/hr | wt % |
| Ethylene | 6861 | 14 | 6859 | 77 | 88 | 0 | 88 | 1 | 86 | 1 | 2 | 1 | 0 | 0 |
| 1-C4 | 1750 | 4 | 1604 | 18 | 8194 | 17 | 8193 | 85 | 8048 | 85 | 145 | 85 | 1 | 0 |
| 1-C6 | 9269 | 19 | 244 | 3 | 10279 | 21 | 1277 | 13 | 1254 | 13 | 23 | 13 | 9002 | 23 |
| Solvent | 20096 | 40 | 127 | 1 | 20022 | 40 | 53 | 1 | 52 | 1 | 1 | 1 | 19969 | 50 |
| Heavy | 10894 | 23 | 24 | 1 | 10871 | 22 | 1 | 0 | 1 | 0 | 0 | 0 | 10870 | 27 |
| Total flow rate | 48870 | 100 | 8858 | 100 | 49453 | 100 | 9611 | 100 | 9441 | 100 | 170 | 100 | 39842 | 100 |

Heavy: a substance having a higher molecular weight than the solvent
Stream 1: the second discharge stream from the reactor 100 which was supplied from the reactor 100 to the second separation device 210
Stream 2: the upper discharge stream from the second separation device 210
Stream 3: the lower discharge stream from the second separation device 210
Stream 4: the upper discharge stream from the third separation device 220
Stream 5: the upper discharge stream from the third separation device 220 which was supplied from the third separation device 220 to the pump 400.
Stream 6: the part of the upper discharge stream from the third separation device 220 which was not supplied to the pump but recovered
Stream 7: the lower discharge stream from the third separation device 220

In the table of the present invention, the flow rates of the components in the stream were indicated by rounding off the numbers to the nearest tenth, and when the flow rate was indicated as wt %, it was calculated as a content of a component flow rate in the total flow rate.

Referring to Table 1, a ratio of the 1-C4 content in the second discharge stream from the reactor 100, which was supplied to the second separation device 210, and the 1-C4 content in the stream circulated through the second separation device 210 and the third separation device 220 and then back to the second separation device 210, that is, a concentration ratio of 1-C4 was about 4.6, and it was confirmed therefrom that the 1-C4 content in the lower discharge stream from the second separation device 210 was 17 wt %. In addition, the 1-C4 content in the stream separated by purging a part of the upper discharge stream from the third separation device 220 was 85 wt % and the content of the ethylene monomer was 1 wt %, and it was found therefrom that a 1-C4 purity was high and there was little loss of the ethylene monomer.

Example 2

The process was performed in the same manner as in Example 1, except that the operation pressure of the second separation device 210 was set at 18 bar and the operation pressure of the third separation device 220 was set at 8 bar. The results are shown in the following Table 2.

TABLE 2

| | Stream 1 | | Stream 2 | | Stream 3 | | Stream 4 | | Stream 5 | | Stream 6 | | Stream 7 | |
|---|---|---|---|---|---|---|---|---|---|---|---|---|---|---|
| Temperature (° C.) | 53 | | 47 | | 160 | | 43 | | 45 | | 43 | | 176 | |
| Pressure (bar) | 30 | | 18 | | 18 | | 8 | | 18 | | 8 | | 8 | |
| Flow rate | kg/hr | wt % | kg/hr | wt % | kg/hr | wt % | kg/hr | wt % | kg/hr | wt % | kg/hr | wt % | kg/hr | wt % |
| Ethylene | 6861 | 14 | 6857 | 77 | 286 | 1 | 286 | 2 | 282 | 2 | 4 | 2 | 0 | 0 |
| 1-C4 | 1750 | 4 | 1615 | 18 | 10023 | 19 | 10023 | 80 | 9888 | 80 | 135 | 80 | 0 | 0 |
| 1-C6 | 9269 | 19 | 237 | 3 | 11188 | 21 | 2185 | 17 | 2156 | 17 | 29 | 17 | 9003 | 23 |
| Solvent | 20096 | 41 | 118 | 1 | 20053 | 38 | 76 | 1 | 75 | 1 | 1 | 1 | 19977 | 50 |
| Heavy | 10894 | 22 | 23 | 0 | 10872 | 21 | 1 | 0 | 1 | 0 | 0 | 0 | 10871 | 27 |
| Total flow rate | 48870 | 100 | 8850 | 99 | 52423 | 100 | 12572 | 100 | 12403 | 100 | 169 | 100 | 39851 | 100 |

Heavy: a substance having a higher molecular weight than the solvent
Stream 1: the second discharge stream from the reactor 100 which was supplied from the reactor 100 to the second separation device 210
Stream 2: the upper discharge stream from the second separation device 210
Stream 3: the lower discharge stream from the second separation device 210
Stream 4: the upper discharge stream from the third separation device 220
Stream 5: the upper discharge stream from the third separation device 220 which was supplied from the third separation device 220 to the pump 400
Stream 6: the part of the upper discharge stream from the third separation device 220 which was not supplied to the pump but recovered
Stream 7: the lower discharge stream from the third separation device 220

Referring to Table 2, when the operation pressure of the second separation device 210 was set at 18 bar and the operation pressure of the third separation device 220 was set at 8 bar, the 1-C4 content in the stream separated by purging a part of the upper discharge stream from the third separation device 220 was 80 wt % and the content of the ethylene monomer was 2 wt %, and it was found therefrom that a 1-C4 purity was high and there was little loss of the ethylene monomer.

In addition, as compared with Example 1, the pressure of the second separation device 210 was high, but the concentration flow and the concentration ratio of 1-C4 was increased by increasing Stream 5, whereby the temperature of the lower discharge stream from the second separation device 210 was operated at 160° C. in the same manner as in Example 1.

Comparative Example

Comparative Example 1

For the process flowchart illustrated in FIG. 2, the process was simulated using an Aspen Plus simulator from Aspen Technology, Inc. Here, the upper discharge stream from the second separation device 210 was a stream passing the condenser (not shown) and the lower discharge stream from the second separation device 210 was a stream passing the reboiler (not shown). In addition, ethylene (C2) was supplied as the monomer at a reaction amount of 20,000 kg/hr or more, the reaction conditions of the reactor 100 were set at a temperature of 53° C. and a pressure of 30 bar, and the operation pressure of the second separation device 210 was set at 15 bar. The results are shown in the following Table 3.

TABLE 3

| | Stream 1-1 | | Stream 2-1 | | Stream 3-1 | |
|---|---|---|---|---|---|---|
| Temperature (° C.) | 53 | | 7 | | 212 | |
| Pressure (bar) | 30 | | 15 | | 15 | |
| Flow rate | kg/hr | wt % | kg/hr | wt % | kg/hr | wt % |
| Ethylene | 6861 | 14 | 46861 | 81 | 0 | 0 |
| 1-C4 | 1750 | 4 | 1600 | 19 | 150 | 0 |
| 1-C6 | 9269 | 19 | 0 | 0 | 9268 | 23 |
| Solvent | 20096 | 41 | 0 | 0 | 20096 | 50 |
| Heavy | 10894 | 22 | 0 | 0 | 10894 | 27 |
| Total flow rate | 48870 | 100 | 8461 | 100 | 40409 | 100 |

Heavy: a substance having a higher molecular weight than the solvent
Stream 1-1: the second discharge stream from the reactor 100 which was supplied from the reactor 100 to the second separation device 210
Stream 2-1: the upper discharge stream from the second separation device 210
Stream 3-1: the lower discharge stream from the second separation device 210

Referring to Table 3, though in Comparative Example 1, the second separation device 210 was operated at 15 bar in the same manner as in Example 1, the temperature of Stream 3-1 which was the lower discharge stream from the second separation device 210 was 212° C., which was found to be significantly higher than 160° C. of Example 1. In addition, in Example 2 in which the operation pressure of the second separation device 210 was higher than 15 bar also, the temperature of the lower discharge stream from the second separation device 210 was 160° C., which was found to be significantly lower than the temperature of Comparative Example 1.

In addition, as compared with Examples 1 and 2 in which the content 1-C4 content in the lower discharge stream from the second separation device 210 was 17 wt % and 19 wt %, respectively, it was confirmed in the Comparative Example that the 1-C4 content in the lower discharge stream from the separation device 210 was less than 0.5 wt %.

As a result, the reason why the temperature of the lower discharge stream from the second separation device 210 in Comparative Example 1 was high in spite of operating the apparatus at the same or lower pressure is considered as being that the third separation device 220 connected to the lower discharge stream from the second separation device 210 was absent and 1-C4 was not concentrated in the lower portion of the second separation device 210 due to the absence of the third separation device 220.

Comparative Example 2

The same process was performed in the same manner as in Comparative Example 1, except that the operation pressure of the second separation device 210 was set at 6 bar for lowering the lower portion temperature of the second separation device 210 to 160° C. as in Example 1. The results are shown in the following Table 4.

TABLE 4

|  | Stream 1-1 | | Stream 2-1 | | Stream 3-1 | |
| --- | --- | --- | --- | --- | --- | --- |
| Temperature (° C.) | 53 | | −16 | | 160 | |
| Pressure (bar) | 30 | | 6 | | 6 | |
| Flow rate | kg/hr | wt % | kg/hr | wt % | kg/hr | wt % |
| Ethylene | 6861 | 14 | 46861 | 81 | 0 | 0 |
| 1-C4 | 1750 | 4 | 1600 | 19 | 150 | 0 |
| 1-C6 | 9269 | 19 | 0 | 0 | 9269 | 23 |
| Solvent | 20096 | 41 | 0 | 0 | 20096 | 50 |
| Heavy | 10894 | 22 | 0 | 0 | 10894 | 27 |
| Total flow rate | 48870 | 100 | 8461 | 100 | 40409 | 100 |

Heavy: a substance having a higher molecular weight than the solvent
Stream 1-1: the second discharge stream from the reactor 100 which was supplied from the reactor 100 to the second separation device 210
Stream 2-1: the upper discharge stream from the second separation device 210
Stream 3-1: the lower discharge stream from the second separation device 210

Referring to Table 4, in Comparative Example 2, the temperature of Stream 3-1 which was the lower discharge stream from the second separation device 210 was lowered to 160° C. as in Example 1, by operating the second separation device 210 at 6 bar; however, in this case, since the pressure of the upper discharge stream from the second separation device 210 which was discharged at 6 bar was increased by about 24 bar for supplying the upper discharge stream to the reactor, it was confirmed that two compressors 300 having a compression ratio of up to 3 times should be generally used as shown in FIG. 3. In addition, since only the pressure of the second separation device 210 was lowered while maintaining the composition of the stream supplied to the second separation device 210, as compared with Example 1, the temperature of Stream 2-1 was also lowered like the lowered temperature of Stream 3-1 to become −16° C. As such, since a refrigerant having a lower temperature level than a refrigerant such as a coolant and an ethylene glycol antifreeze which are generally used in the process should be used for cooling the upper discharge stream from the second separation device 210 to −16° C., there is a problem of separate investment costs and operating costs.

The invention claimed is:

1. A method for preparing an oligomer, the method comprising:
   supplying a feed stream including a monomer to a reactor to perform an oligomerization reaction;
   supplying a first discharge stream from the reactor to a first separation device and supplying a second discharge stream from the reactor to a second separation device;
   recovering the monomer as an upper discharge stream from the second separation device and supplying a lower discharge stream from the second separation device to a third separation device; and
   supplying an upper discharge stream from the third separation device to the second separation device.

2. The method for preparing an oligomer of claim 1, wherein the upper discharge stream from the third separation device is a liquid stream including a C4 compound.

3. The method for preparing an oligomer of claim 2, wherein a part of the upper discharge stream from the third separation device is not supplied to the second separation device but recovered.

4. The method for preparing an oligomer of claim 3, wherein a content of the C4 compound included in the part of the upper discharge stream from the third separation device is 70 wt % or more.

5. The method for preparing an oligomer of claim 3, wherein a content of the monomer included in the part of the upper discharge stream from the third separation device is 5 wt % or less.

6. The method for preparing an oligomer of claim 1, wherein the lower discharge stream from the second separation device comprises a C4 compound in an amount of 5 wt % to 40 wt %.

7. The method for preparing an oligomer of claim 1, wherein the upper discharge stream from the third separation device and the second discharge stream from the reactor include a C4 compound, and wherein a ratio of the content of the C4 compound included in the upper discharge stream from the third separation device to the content of the C4 compound included in the second discharge stream from the reactor is 2 or more.

8. The method for preparing an oligomer of claim 1, wherein the second separation device is operated at a higher pressure than the third separation device.

9. The method for preparing an oligomer of claim 8, wherein the pressure in the second separation device is 12 bar to 25 bar and the pressure in the third separation device is 3 bar to 15 bar.

10. The method for preparing an oligomer of claim 1, wherein a temperature of the lower discharge stream from the second separation device is 130° C. to 200° C.

11. The method for preparing an oligomer of claim 1, wherein the monomer is ethylene and the oligomer is an alpha-olefin.

12. An apparatus for preparing an oligomer comprising:
   a reactor for oligomerizing a feed stream including a monomer, supplying a first discharge stream to a first separation device, and supplying a second discharge stream to a second separation device;
   the first separation device for being supplied with the first discharge stream from the reactor;
   the second separation device for being supplied with the second discharge stream from the reactor to recover the monomer as an upper discharge stream and to supply a lower discharge stream to a third separation device; and the third separation device for being supplied with the lower discharge stream from the second separation device to supply an upper discharge stream to the second separation device.

* * * * *